United States Patent [19]

Alvarado

[11] Patent Number: 4,583,670

[45] Date of Patent: Apr. 22, 1986

[54] SURGICAL STAPLING

[76] Inventor: Alfredo Alvarado, 1974 Heritage Rd., Huntingdon Valley, Pa. 19006

[21] Appl. No.: 565,086

[22] Filed: Dec. 23, 1983

[51] Int. Cl.[4] ............... A61B 17/00; A61B 17/04; A61B 17/10

[52] U.S. Cl. ........................ 227/19; 227/83

[58] Field of Search ............ 227/19, DIG. 1, 83; 128/334 R

[56] References Cited

U.S. PATENT DOCUMENTS

| | | | |
|---|---|---|---|
| 2,707,783 | 5/1955 | Sullivan | 227/DIG. 1 |
| 2,817,339 | 12/1957 | Sullivan | 128/334 |
| 2,853,074 | 9/1958 | Olson | 128/322 |
| 3,144,654 | 8/1964 | Mallina et al. | 227/19 |
| 3,244,342 | 4/1966 | Boorlakov et al. | 227/DIG. 1 |
| 3,601,302 | 8/1971 | Potekhina et al. | 227/120 |
| 3,780,416 | 12/1973 | Rider | 29/212 D |
| 4,122,989 | 10/1978 | Kapitanov et al. | 227/108 |
| 4,179,057 | 12/1979 | Becht et al. | 227/19 |
| 4,375,866 | 3/1983 | Giersch et al. | 227/19 |
| 4,399,810 | 8/1983 | Samuels et al. | 227/19 X |

*Primary Examiner*—Paul A. Bell
*Attorney, Agent, or Firm*—Seidel, Gonda, Goldhammer & Abbott

[57] ABSTRACT

A surgical stapler for forming and implanting surgical staples in the skin or fascia of a patient to close a wound or incision is provided and comprises a member having a rearward portion including a handle portion and a forward portion having a front surface facing the incision, and a guide disposed at the forward-most end of the forward portion which guide is inserted beneath the surface of the skin or fascia and plows through the incision to be stapled.

9 Claims, 21 Drawing Figures

SURGICAL STAPLING

BACKGROUND OF THE INVENTION

This invention relates to surgical stapling. More particularly, the present invention concerns surgical stapling instruments, surgical staples and suturing methods.

Recently surgeons have turned to the use of surgical staples (sometimes referred to as stable sutures), rather than conventional thread sutures, for closing of wounds or incisions in the skin or fascia of a patient. This is due in part because the use of surgical staples is a far easier procedure as compared to the employment of thread sutures. Of even greater importance, however, is a fact that the use of surgical staples is much faster than the use of thread sutures. Thus, the time required for suturing can be substantially reduced, thereby reducing the length of time the patient must be maintained under anesthesia.

Various types of surgical stapling instruments have been developed, examples of which are described in the following U.S. Pat. Nos.: 2,853,074; 3,144,654; 3,269,630; 3,601,302; 3,717,294; 3,780,416; 3,837,555; 3,873,016; 4,109,844; 4,122,989; 4,179,057; 4,185,762; and 4,296,881.

U.S. Pat. Nos. 4,043,504 and 4,127,227 describe cartridges for use in surgical staplers.

U.S. Pat. No. 4,180,196 concerns an anvil attachment for a surgical stapling instrument.

Disposable skin staplers are sold by various companies such as Davis+Geck of Wayne, N.J. and Ethicon, Inc. of New Jersey.

U.S. Pat. No. 4,265,226 relates to a surgical clip for closing an incision. U.S. Pat. No. 2,817,339 is directed to a rigid fascial suture.

In order for incisions in the skin to heal properly, the torn edges of the skin must be upbutted edge to edge. Conventional skin staplers, however, tend to invert the skin. In other words, skin is bent down such that the edges do not abut. Healing therefore fails to take place. One aspect of the present invention is to alleviate this problem by everting the skin during suturing.

Conventional stapling instruments are cumbersome to use. Generally suturing skin with such devices requires at least two people. One person is required to hold the torn skin together by use of forceps, one forcep in each hand to hold each piece of skin. Another person is required to operate the stapling instrument.

The present invention allows for a two-hand stapling operation by the use of a guide which helps to keep the stapling instrument on the mid-line between the two pieces of torn skin. Conventional stapling instruments generally require the user, such as a surgeon, to proceed in a backward manner and to pull back on a stapling instrument to free the staple from the stapling device after insertion of a staple in the skin of a patient. The present invention allows for the operation of the surgical stapler in a forward manner without the need for any back-movement to free the inserted staple.

SUMMARY OF THE INVENTION

The present invention concerns a surgical stapler for implanting and forming substantially rigid surgical staples to suture an incision in the skin or fascia of a patient. The stapler comprises a member having a rearward portion including a handle portion and a forward portion. The forward portion of the stapler has a front surface facing the incision, a staple-folding anvil disposed at the end of the forward portion and within the member, a pusher disposed above the anvil and movable toward the anvil for pushing a staple through the skin or fascia to be stapled and against the anvil, and a guide disposed at the forward-most end of the forward portion and attached to the member. The guide includes an upright member which protrudes below the bottom of the forward portion and a base attached at the bottom end of the upright member. The base of the guide has a front facing the incision. The guide is shaped and of such dimensions to permit the base to be inserted beneath the surface of the skin or fascia and to permit the upright member to readily fit between the incision so as to allow the guide to plow through the incision.

The present invention also relates to a surgical staple for suturing skin or fascia. The staple comprises a relatively rigid body. The body includes a substantially horizontally-extending upper member terminating at the ends thereof in downturned side members. The side members are disposed at an included angle from the upper member of between about 85° and about 75°. The side members are beveled at their ends thereof so as to form outwardly angular tissue-penetrating prongs. The staple, when stapled into the skin or fascia, has a pair of inwardly-directed lower members which are upturned toward the horizontally-extending upper member such that the ends of each lower member are substantially close to one another and such that each lower member is disposed at an angle from the horizontal of between about 5° and about 20°, so as to evert the sutured skin or fascia.

This invention is also directed to a method of suturing an incision in skin or fascia. The method includes inserting at least one substantially rigid surgical staple across an incision in the skin or fascia. The staple, when inserted in the skin or fascia, has a substantially horizontally-extending upper member disposed above the skin or fascia being sutured, side members at opposite ends of the upper member and generally disposed at an angle of between about 75° and about 95° from the upper member. The side members pierce the skin or fascia. The staple has lower members extending from each side member. The lower members are in the same plane as the upper member and the lower members are disposed below the skin or fascia being sutured. The method further includes bending the side members and lower members such that the lower members are at an angle from the horizontal of between about 5° and about 20°.

The present invention also relates to an anvil for a surgical stapler. The anvil serves to implant staples in the skin or fascia of a patient and bend staples initially having a substantially horizontally-extending upper member and side members at opposite ends of the upper member, the side members disposed at an included angle from the upper member of between about 85° and about 75°, to a bent configuration having lower members extending from each side member with the lower members in the same plane as the upper member and the lower members bent upward at an angle from the horizontal of between about 5° and about 20° when implanted. The anvil includes a substantially horizontally extending member to support the upper member of the staple. A pusher is disposed above the anvil and movable toward the anvil for pushing a staple through the skin or fascia to be stapled and against the anvil.

A BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

While the stapling instrument and staples of the present invention may have many applications, such are particularly adapted for use in surgical stapling and will, for purposes of an exemplary showing, be so described hereinafter. A surgical stapling instrument of the present invention could be so constructed as to be reusable. Nevertheless, the surgical stapler of this invention is particularly well-adapted to be inexpensively produced as a single-use, disposable instrument, and for that reason will be so described hereinafter for purposes of an exemplary showing.

In all of the Figures, like parts have been given like numerals. Reference is first made to FIGS. 1 to 4.

Figure 1:
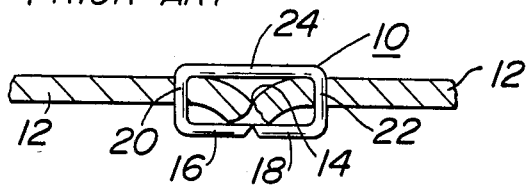
FIG. 1 is an elevational view partly in cross-section showing a prior art staple and the use of same for suturing skin.

In FIG. 1, a prior art staple 10 is depicted in its fully-formed condition and implanted in the skin 12 of a patient to suture wound 14. In its fully formed condition, the legs 16 and 18 of the staple are in-turned and opposed. Portions 20 and 22 of original crown 24 are bent downwardly. This downward bending is accomplished by a staple pusher which bends legs 16 and 18 about an anvil surface of a stapler. As shown in FIG. 1, conventional staple configuration 10 inverts the skin 12, thus hampering healing of the wound 14.

Figure 2:
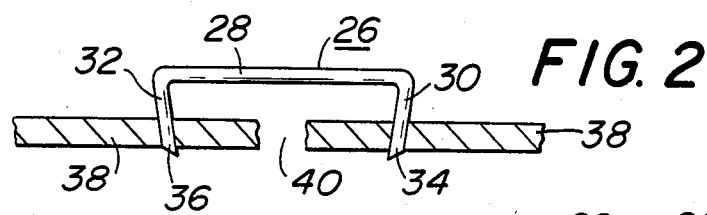
FIG. 2 is an elevational view partly in cross-section showing a staple according to the present invention piercing the torn skin of an incision of a patient.
Figure 3:
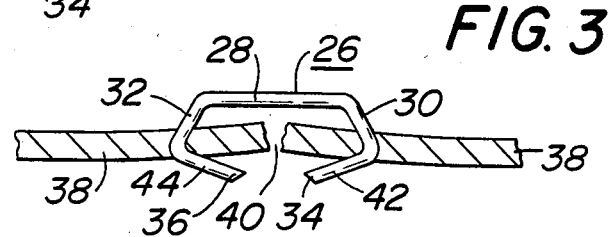
FIG. 3 is an elevational view partly in cross-section of the staple shown FIG. 2 in a partially-formed configuration.
Figure 4:
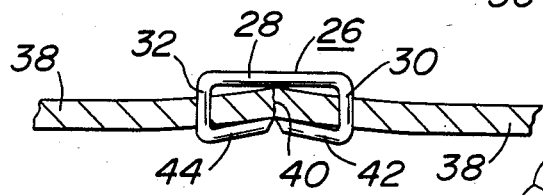
FIG. 4 is an elevational view partly in cross-section of the staple shown in FIG. 2 in a fully-formed configuration, implanted in the skin of the patient.

In FIGS. 2 to 4, a staple configuration according to the present invention in various degrees of its formation is depicted.

In FIG. 2, the initial staple configuration of staple 26 of the present invention is shown. Staple 26 has a crown 28 and crown sections 30 and 32 which terminate in tissue-penetrating prongs 34 and 36. Crown sections 30 and 32 are disposed at an included angle from the crown 28 of between about 85° and about 75°. Staple 26 pierces the skin 38 to close the wound 40.

In FIG. 3, by the pushing of staple 26 against an anvil surface in a stapler (not shown), the crown sections 30 and 32 are bent to form legs 42 and 44.

FIG. 4 depicts the fully-formed configuration of a staple 26 with the crown 28 disposed above the skin 38 and crown portions 30 and 32 piercing the skin 38. Legs 42 and 44 are bent slightly upward at an angle from the horizontal of between about 5° and about 20°, preferably between about 7° and about 15°. Staple 28 serves to evert the skin 38 at the point of the wound 40.

Figure 5:
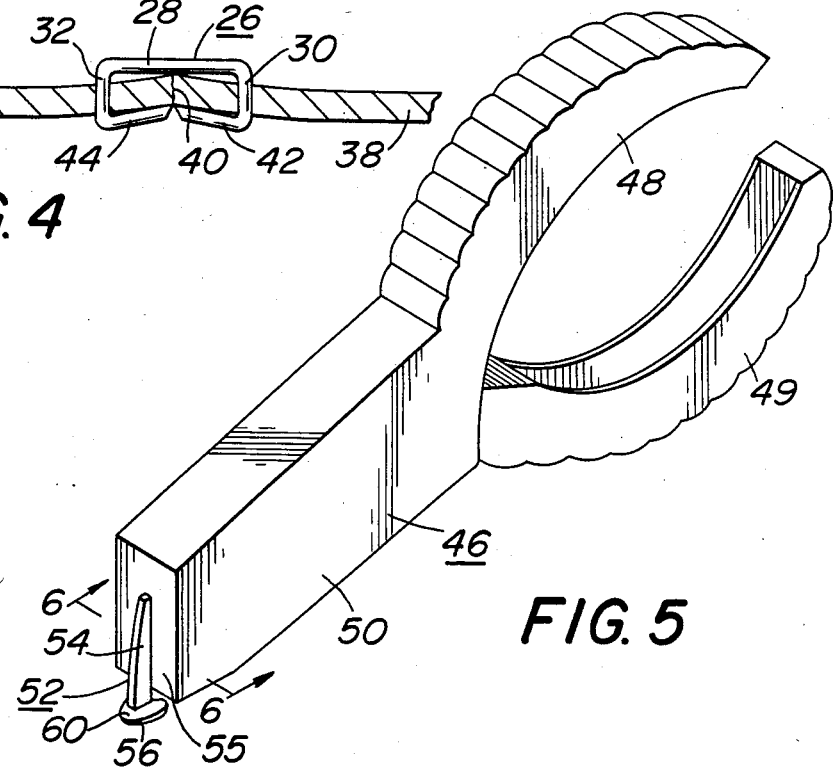
FIG. 5 is a perspective view of a surgical stapler according to the present invention.
Figure 6:
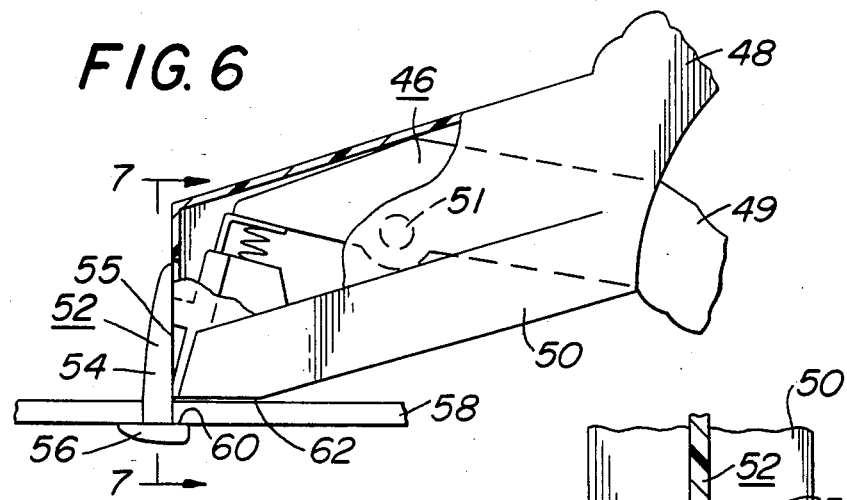
FIG. 6 is a fragmentary side-elevational view of a stapler employing a stapling guide according to the present invention.

In FIGS. 5 and 6, a stapler 46 is depicted having rear handles 48 and 49 and a forward portion 50. A pivot pin 51 connects handles 48 and 49 together and to the forward portion 50.

A guide 52 is disposed at the forward-most end of the forward portion 50. Guide 52 has an upright member 54 and a base 56 attached at the bottom of the upright member 54.

The transverse dimension of base 56 at the point where base 56 meets upright member 54 is greater than the transverse dimension of the upright member 54. The base 56 is tapered towards its front.

The base 56 has an included angle in relation to the front surface 55 of the stapler 46 of at least about 80°. The distance from the top surface 60 of the base 56 to the bottom surface 62 of the stapler 46 is between about two sixteenths of an inch and about three quarters of an inch. The front of the base 56 is rounded.

Figure 7:
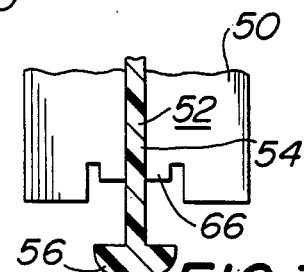
FIG. 7 is a cross-sectional view taken along the line 7—7 of FIG. 6.

In FIG. 7, the anvil 66 is shown in relation to the guide 52.

Figure 8:
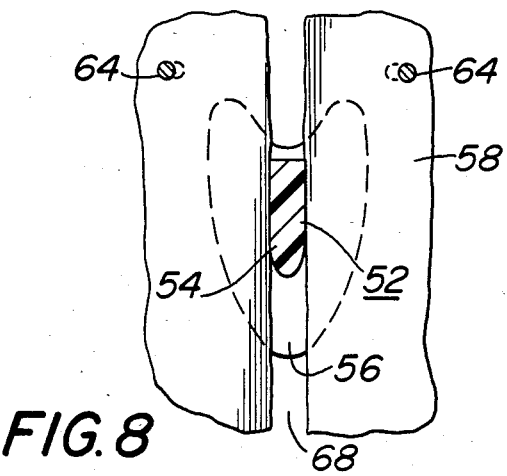
FIG. 8 is a top plan view showing a stapling guide of a stapler according to the present invention with the guide disposed in the skin and a staple piercing the skin, such staple as depicted in FIG. 2.
Figure 9:
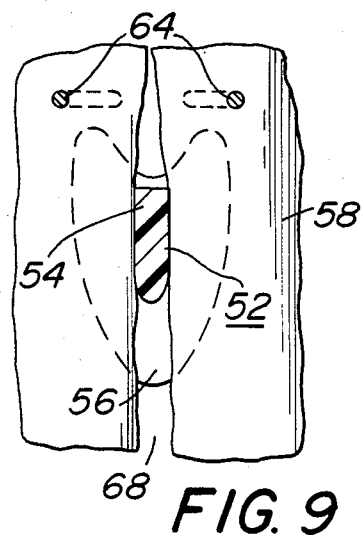
FIG. 9 is a top plan view similar to FIG. 8 and showing a staple configuration as depicted in FIG. 3.
Figure 10:
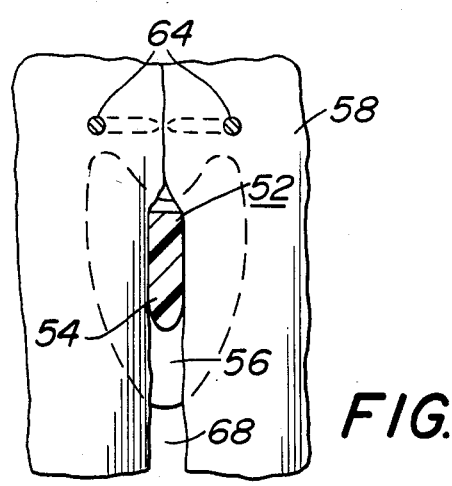
FIG. 10 is a top plan view similar to FIG. 8 and showing a staple configuration as depicted in FIG. 4.

FIGS. 8 to 10 depict the guide 52 in relation to the forming of the staple 64 in skin 58 to close incision 68.

Figure 11:
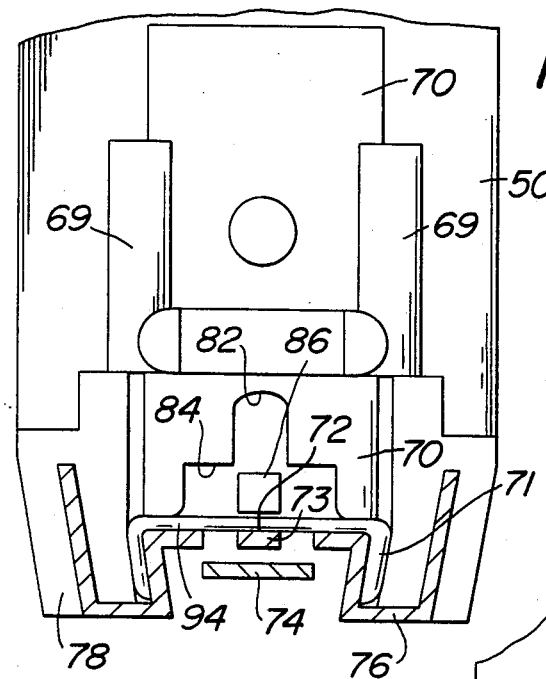
FIG. 11 is a fragmentary front sectional view of the forward section of a stapler employing the staple as depicted in FIG. 2, illustrating the staple pusher in the retracted position.

FIG. 11 is a fragmentary front sectional view of the stapler 46 showing the staple pusher 70 in its retracted position and staple 71 having an initial configuration as shown in FIG. 2 mounted on surface 72 of the springing extension 73 of rail 76. Staple pusher 70 reciprocates along grooves (not shown) in guide members 69 in forward portion 50 of the stapler. The rail 76 is located on the underside of the instrument beneath the stapler magazine 78.

Rail 76 is designed to accomodate a row of staples, either bonded together or in a cartridge. Rail 76 has two parallel grooves spaced for accomodating the legs of staple 71. Rail 76 has a horizontal platform member for supporting the crown portion of the staple. The two parallel grooves are slanted inward at an included angle from the horizontal of between about 75° and about 85°, corresponding to the included angle betwen the crown and leg portions of an unformed staple according to the present invention.

The stapler pusher 70 comprises an elongated plate preferably fabricated of a metal suitable for a surgical environment. An example of such metal is stainless steel. The pusher 70 is provided with a series of notches 82 and 84. Notch 84 is so sized as to cause the forming of a staple 71 about anvil 74. Anvil 74 is located on an L-shaped extension of anvil body 90 (not shown). Notch 82 serves as a clearance notch for lug 86 which is at the forward end of magazine 78. Lug 86 serves as a guide for pusher 70 to keep it centered during stapling.

Figure 12:
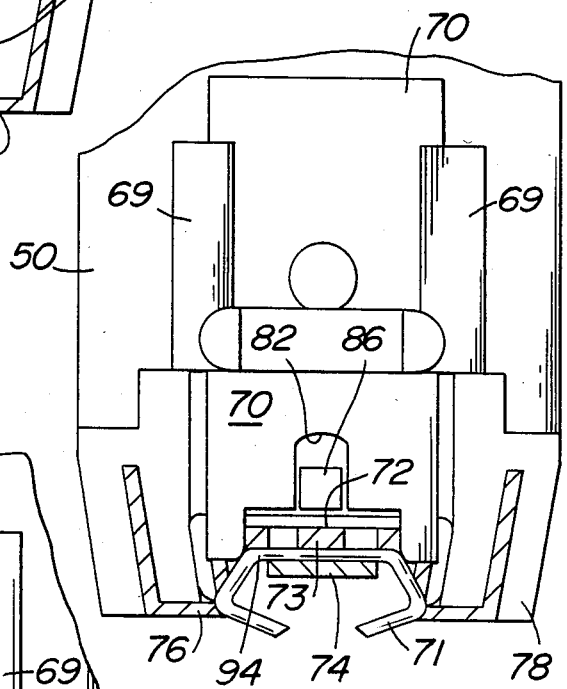
FIG. 12 is a fragmentary front-sectional view similar to FIG. 11, showing a staple configuration as depicted in FIG. 3.
Figure 13:
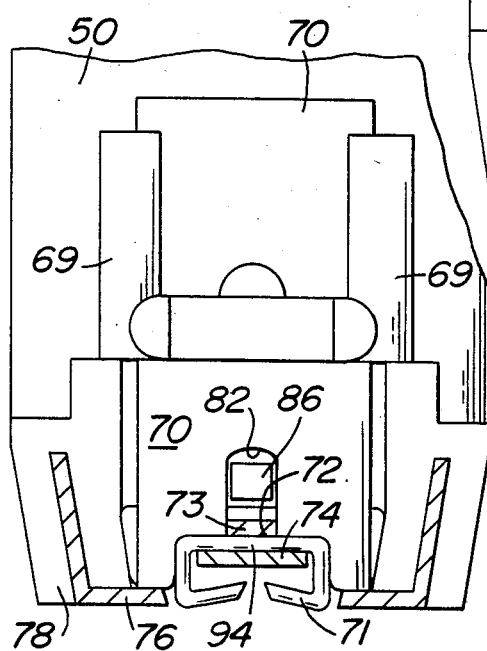
FIG. 13 is a fragmentary front-sectional view similar to FIG. 11, showing a staple configuration in FIG. 4, and illustrating the staple pusher in its staple-forming position.

FIGS. 12 and 13 differ from FIG. 11 only in that staple 71 has been delivered from springing extension 73 of rail 76 onto anvil 74, and that the staple pusher 70 is depicted in an intermediate staple-forming position in FIG. 12 and in a completed staple-forming position in FIG. 13.

In operation, when handles 48 and 49 are squeezed towards each other, a spring-biased trigger mechanism engages a staple pusher actuator (not shown). The actuator exerts a downward force on a staple pusher 70 to fully form staple 71. Simultaneously with the forming of staple 71, staples held in magazines 78 are fed one at a time onto the surface 72 of springing extension 73 of rail 76. After each staple delivery onto surface 72, the next stroke of staple pusher 70 forces springing extension 73 of rail 76 downward, transferring the staple onto anvil 74. As the staple pusher 70 continues downward, the staple is formed around anvil 74. The operation of a surgical stapler is described in greater detail in several patents, such as, for example, U.S. Pat. No. 4,179,057.

Figure 14:
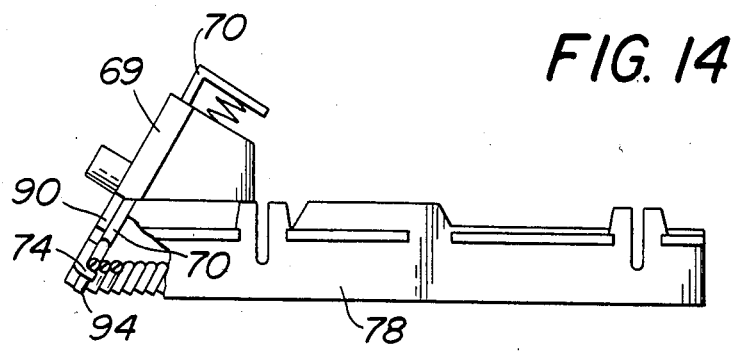
FIG. 14 is a fragmentary side-elevational view of the staple cartridge and staple rail according to the present invention.

FIG. 14 is a fragmentary side-elevational view showing staple cartridge 78 with rail 76 removed. A row of staples 94 rests in cartridge 78 with the forward-most staple 94 resting on anvil 74. Anvil 74 is an L-shaped extension of anvil body 90. Above the forward-most staple 94 is staple pusher 70. Staple pusher 70 is reciprocated in grooves in guide member 69 for bending staples 94.

Figure 15:
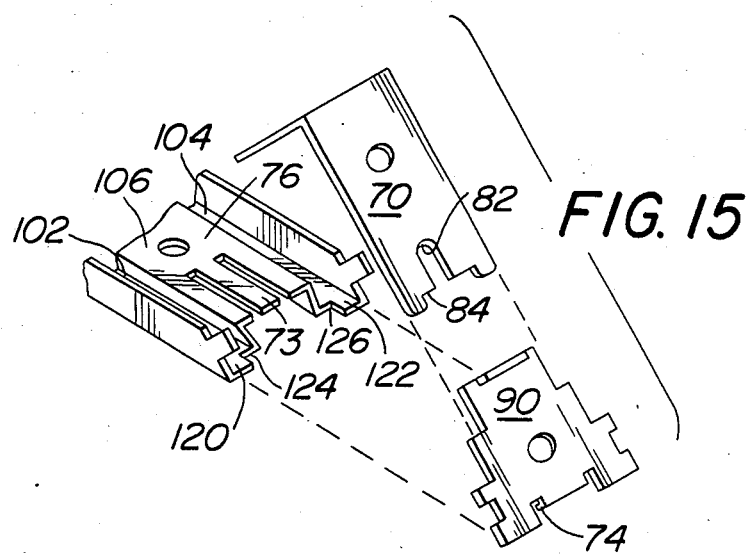
FIG. 15 is an exploded perspective view showing the rail, pusher and anvil.
Figure 16:
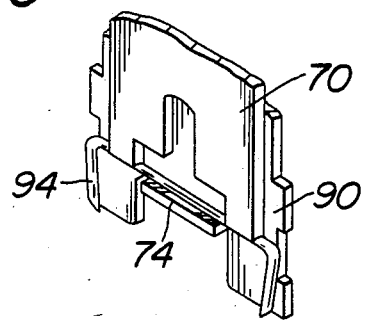
FIG. 16 is a fragmentary perspective view showing the pusher, anvil and staple as depicted in FIG. 11.
Figure 17:
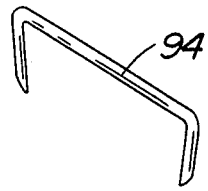
FIG. 17 is a perspective view showing the staple configuration as depicted in FIG. 11.
Figure 18:
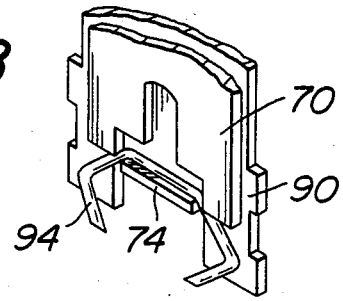
FIG. 18 is a fragmentary perspective view showing the pusher, anvil and staple as depicted in FIG. 12.
Figure 19:
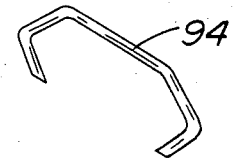
FIG. 19 is a perspective view showing the staple configuration as depicted in FIG. 12.
Figure 20:
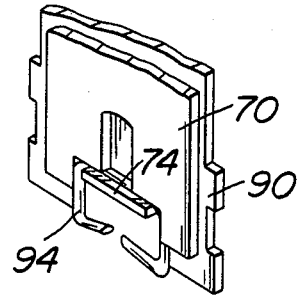
FIG. 20 is a fragmentary perspective view showing the pusher, anvil and staple as depicted in FIG. 13.
Figure 21:
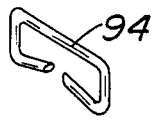
FIG. 21 is a perspective view showing the staple configuration as depicted in FIG. 13.

FIG. 15 is an exploded view showing rail 76, anvil body 90 and pusher 70. Rail 76 has two parallel grooves 102 and 104 for accomodating the legs of staples 94 (not shown). The horizontal platform member 106 of rail 76 supports the crown portions of staples 94. Grooves 102 and 104 are angled inwardly at an angle from the horizontal of between about 75° and about 85°, corresponding to the included angle between the crown and legs of unformed staples 94.

Rail 76 terminates in an end portion facing anvil body 90 as shown in FIG. 15. Grooves 102 and 104 terminate in legs 120 and 122. The legs 120 and 122 are on either side of the springing extension 73 of horizontal platform member 106 and are disposed a distance below the extension 73. The legs 120 and 122 are separated from each other by a distance such that the inner surfaces of the legs 120 and 122 define recesses 124 and 126.

FIGS. 16 through 21 show the bending of staple 94 on anvil 74 in a similar manner as shown in FIGS. 11-13 respectively.

The present invention may be embodied in other specific forms without departing from the spirit or essential attributes thereof and, accordingly, reference should be made to the appended claims, rather than the foregoing specification, as indicating the scope of the invention.

I claim:

1. A surgical stapler for implanting and forming substantially rigid surgical staples to suture an incision in the skin or fascia of a patient comprising a member having a rearward portion including a handle portion and a forward portion, said forward portion having a front surface facing the incision, a staple-folding anvil disposed at the end of said forward portion and within said member, a pusher disposed above said anvil and movable toward said anvil for pushing a staple through the skin or fascia to be stapled and against said anvil, and a guide disposed at the forward-most end of said forward portion and attached to said member, said guide comprising an upright member which protrudes below the bottom of said forward portion and a base attached at the bottom end of said upright member, said base having a front facing the incision, said guide being shaped and of such dimensions to permit said base to be inserted beneath the surface of the skin or fascia and to permit said upright member to readily fit between the incision so as to allow said guide to plow through the incision.

2. A surgical stapler according to claim 1 wherein said base of said guide is generally triangular-shaped with the point of the triangle facing the front of said base.

3. A surgical stapler according to claim 1 wherein the transverse dimension of said base at the point where said base meets said upright member is greater than the transverse dimension of said upright member.

4. A surgical stapler according to claim 1 wherein said base is tapered toward its front.

5. A surgical stapler according to claim 1 wherein said base has an included angle in relation to said front surface of at least about 80°.

6. A surgical stapler according to claim 1 wherein the distance from the top surface of said base to the bottom of the forward portion is between about 2/16 inch and about ¾ inch.

7. A surgical stapler according to claim 1 wherein the front of said base is rounded.

8. A surgical stapler for implanting and forming substantially rigid surgical staples to suture an incision in the skin or fascia of a patient, said staples initially having substantially horizontally-extending upper member and side members at opposite ends of the upper member disposed at an included angle from said upper member of between about 85° and about 75°, the stapler having an anvil for bending the staple to a configuration having lower members extending from each side member with said lower members in the same plane as the upper member and said lower members bent upward at an angle from the horizontal of between 5° and about 20° when implanted, the stapler comprising a member having a rearward portion including a handle portion and a forward portion, said forward portion having a front surface adapted to face the incision, a staple-holding rail on the underside of said forward portion comprising a horizontally-extending platform member disposed between two parallel grooves spaced for holding unformed staples, with the anvil disposed at the end of said forward position, a pusher disposed above said anvil and movable toward said anvil for pushing a staple through the skin or fascia to be stapled and against said anvil, and a guide at the forward-most end of said forward portion, said guide comprising an upright member which protrudes below the bottom of said forward portion and a base attached at the bottom end of said upright member, said base having a front facing the incision, said guide being shaped and of such dimensions to permit said base to be inserted beneath the surface of the skin or fascia and to permit said upright member to readily fit between the incision so as to allow said guide to plow through the incision.

9. A surgical stapler according to claim 8 wherein the parallel grooves of the staple holding rail are slanted inwardly at an included angle from the horizontal between about 75° and about 85°.

* * * * *